(12) United States Patent
Li

(10) Patent No.: US 12,582,570 B2
(45) Date of Patent: Mar. 24, 2026

(54) FAST-CONNECTED LABORATORY ANIMAL TEST BENCH

(71) Applicant: Qingdao Hilai Machinery Manufacture Co., Ltd., Qingdao (CN)

(72) Inventor: Shousheng Li, Qingdao (CN)

(73) Assignee: Qingdao Hilai Machinery Manufacture Co., Ltd., Qingdao (CN)

( * ) Notice: Subject to any disclaimer, the term of this patent is extended or adjusted under 35 U.S.C. 154(b) by 455 days.

(21) Appl. No.: 18/201,220

(22) Filed: May 24, 2023

(65) Prior Publication Data

US 2024/0252300 A1     Aug. 1, 2024

(30) Foreign Application Priority Data

Jan. 29, 2023     (CN) ........................ 202310086968.X

(51) Int. Cl.
| | |
|---|---|
| *A61G 13/10* | (2006.01) |
| *A61D 3/00* | (2006.01) |
| *A61B 16/00* | (2006.01) |

(52) U.S. Cl.
CPC ............. *A61G 13/102* (2013.01); *A61D 3/00* (2013.01); *A61B 16/00* (2013.01)

(58) Field of Classification Search
CPC ......... A61G 13/00; A61G 13/102; A61D 3/00
See application file for complete search history.

(56) References Cited

U.S. PATENT DOCUMENTS

| | | | | |
|---|---|---|---|---|
| 1,475,143 A * | 11/1923 | Schellberg | ............. | A61G 13/00 |
| | | | | 5/606 |
| 5,454,797 A * | 10/1995 | Haswell | ................. | A61B 50/33 |
| | | | | 604/317 |
| 6,279,510 B1 * | 8/2001 | Batterton | ................. | A61D 3/00 |
| | | | | 119/753 |
| 6,467,112 B1 * | 10/2002 | Cheng | ...................... | A61D 3/00 |
| | | | | 5/606 |
| 2008/0127417 A1 * | 6/2008 | Harty | ................... | A61G 13/102 |
| | | | | 5/606 |
| 2022/0265411 A1 * | 8/2022 | Reback | .................... | A61D 3/00 |

(Continued)

FOREIGN PATENT DOCUMENTS

| | | | | | |
|---|---|---|---|---|---|
| CN | 107126292 A | * | 9/2017 | ........... | A61G 13/102 |
| CN | 109528426 A | * | 3/2019 | ......... | A61G 13/0027 |
| CN | 111990970 A | * | 11/2020 | ........... | A61B 5/4343 |

(Continued)

*Primary Examiner* — Michael H Wang
(74) *Attorney, Agent, or Firm* — Birchwood IP

(57) ABSTRACT

The present application provides a fast-connected laboratory animal test bench, which belongs to the technical field of experimental supplies, and comprises a test bench, a liquid storage tank and a plurality of fixing bolts, and the fixing bolts are all arranged on the test bench, and is able to bind ropes to fix animals, wherein, the test bench is provided with a liquid discharge groove located inside a range surrounded by all the fixing bolts, and the liquid storage tank is arranged at a bottom of the test bench and is configured to accommodate the waste liquid discharged from the liquid discharge groove. The overall structure of the present application is relatively simple. The animals to be tested are tied up with ropes, and the ropes are bound to the fixing bolts. The bound animals are located above the liquid discharge groove on the upper part of the test bench.

4 Claims, 8 Drawing Sheets

(56)    References Cited

U.S. PATENT DOCUMENTS

2023/0076432 A1 *   3/2023   Skinner .................. A01K 13/00
2025/0170007 A1 *   5/2025   Pretorius .............. A61G 13/108

FOREIGN PATENT DOCUMENTS

CN          113101106 A  *  7/2021   ............... A61G 9/02
CN          113244076 A  *  8/2021   ......... A61G 13/0027
CN          116983115 A  *  11/2023   ............... A61D 3/00

* cited by examiner

FAST-CONNECTED LABORATORY ANIMAL TEST BENCH

CROSS-REFERENCE TO RELATED APPLICATIONS

This application claims the benefit and priority of Chinese patent application No. 202310086968.X, filed on Jan. 29, 2023, disclosure of which is hereby incorporated by reference in its entirety.

TECHNICAL FIELD

The application relates to the field of laboratory supplies, in particular to a fast-connected laboratory animal test bench.

BACKGROUND

The animal anatomy experiment is used to help students deepen their understanding of the shape, location and structure of the main organs of the animal body, help students distinguish the characteristics of the tissue structure of different animals, and establish a macroscopic understanding of the animal body. Animal anatomy experiments are inseparable from the test bench.

For example, a test bench for animal physiological anatomy disclosed in the Chinese Utility Model Patent Application No. CN202120302919.1, which mainly includes a test bench, a collection box, and a bottom plate. One end of the bottom of the test bench is hinged on the fixed block on the bottom plate, and a lifting structure is provided between the other end and the bottom plate. When processing waste liquid and waste on the test bench, the manual operation of the lifting structure makes the test bench in a state of high left and low right, which facilitates the transfer of waste liquid and waste on the test bench to the collection box at the right end.

The above test bench has the following technical problems:

1. The test bench has a large shape and complex structure.
2. It is easy to drop waste liquid and waste from the test bench, but it is difficult to quickly remove these waste liquid and waste by the waste liquid treatment method adopted in the above solution.

SUMMARY

In order to make up for the above deficiencies, the present application provides a fast-connected laboratory animal test bench. Through the following structural design, the above technical problems are well solved, and the purpose or effect of reducing costs and improving the cleaning efficiency of the test bench is achieved.

The embodiment of the present application provides a fast-connected laboratory animal test bench, comprising a test bench and a liquid storage tank and a plurality of fixing bolts, and the fixing bolts are all arranged on the test bench, and is able to bind ropes to fix animals, the test bench is provided with a discharge groove located inside a range surrounded by all the fixing bolts, the liquid storage tank is arranged at bottom of the test bench and is configured to accommodate waste liquid discharged from the liquid discharge groove.

In a specific embodiment, the fixing bolt is divided into an upper and a lower section, an outer wall of the lower section is provided with external threads, and an outer wall of the upper section is configured to be smooth, and a plurality of bolt fixing holes are correspondingly formed on the test bench, the lower section of the fixing bolt is screwed into the corresponding bolt fixing hole.

In the above implementation process, after the fixing bolt is fixed to the test bench through the bolt fixing hole, it can be equivalent to the role of the fixing pile, which facilitates the binding of the rope.

In a specific embodiment, a liquid discharge port communicating with the liquid discharge groove is formed in the test bench, and the waste liquid in the liquid discharge groove is led to the inside of the liquid storage tank through the liquid discharge port.

In the above implementation process, the liquid discharge port is used as an intermediate connection hole, which is beneficial to quickly lead the waste and liquid accumulated in the liquid discharge groove to the liquid storage tank through the liquid discharge port, so as to realize the collection and cleaning of waste and waste liquid.

In a specific embodiment, an annular protrusion is provided at an outer edge of a bottom end surface of the test bench around the liquid discharge port, and a connecting piece located on an outer periphery of the annular protrusion is arranged on the bottom end surface of the test bench, an outer wall of a bottle mouth of the liquid storage tank is provided with external threads, and is screwed with the connecting piece through the external threads.

In the above implementation process, the connecting piece facilitates the fixing of the liquid storage tank and the test bench, so that the waste liquid on the test bench can be quickly discharged into the liquid storage tank.

In a specific embodiment, the connecting piece comprises:

an annular ring, located on the outer periphery of the annular protrusion;

two lugs, connected to both symmetrical sides of the annular ring, and fixed to the bottom end surface of the test bench;

two internally threaded sleeves, respectively connected to an inner and outer sides of an outer surface of the annular ring, there is a distance between the internally threaded sleeves, and there is also a distance between the internally threaded sleeve located on the inner side and an outer ring of the annular protrusion, the bottle mouth of the liquid storage tank is connected with one of the internally threaded sleeves.

In the above implementation process, when the connecting piece is operated, the lugs are fixed to the bottom end surface of the test bench by screws, and the two internally threaded sleeves after fixing are located on the outer ring of the annular protrusion and do not contact it. The bottle mouth of the liquid storage tank can be screwed with the inner ring of the matching internally threaded sleeve. On the contrary, it is to use the design of two internally threaded sleeves to facilitate the installation of different liquid storage tanks, and the installation applicability is higher.

In a specific embodiment, the test bench is formed in the shape of a rectangular plate, and the four corners are rounded and chamfered.

In the above implementation process, the discomfort caused by the user accidentally bumping into the corner of the test bench is reduced.

In a specific embodiment, at a middle position of the bottom of the test bench is provided with rectangular bumps integrally formed with it, and a mounting groove is arranged inside the rectangular bump, and a vertical cross-sectional shape of the mounting groove is an inverted T-shape.

In the above implementation process, the external legs can be inserted into the mounting grooves of the rectangular bumps to facilitate the fixing of the test bench. The shape of the specific external leg design may include the shape of the base and the middle column. The middle column is fixed in the middle of the upper end of the base, and the shape of the top of the middle column is adapted to the mounting groove. Other suitable shapes can also be selected for the external legs, which are not limited here.

Beneficial effect: The present application provides a fast-connected laboratory animal test bench. The overall structure of the present application is relatively simple. The animals to be tested are tied up with ropes, and the ropes are bound to the fixing bolts. The bound animals are located above the liquid discharge groove on the upper part of the test bench. During the animal experiment, the residual liquid waste will fall directly into the discharge groove, and finally collect into the liquid storage tank. It solves the problem that it is difficult to quickly remove waste liquid and waste on the test bench, and is conducive to the rapid recovery of the test environment.

BRIEF DESCRIPTION OF DRAWINGS

In order to more clearly illustrate the technical solutions of the embodiments of the present application, the following will briefly introduce the drawings that need to be used in the embodiments. It should be understood that the following drawings only illustrate certain embodiments of the application, and thus should not be considered as limiting the scope. For those skilled in the art, other related drawings can also be obtained based on these drawings without creative effort.

REFERENCE SIGNS

Figure 1:
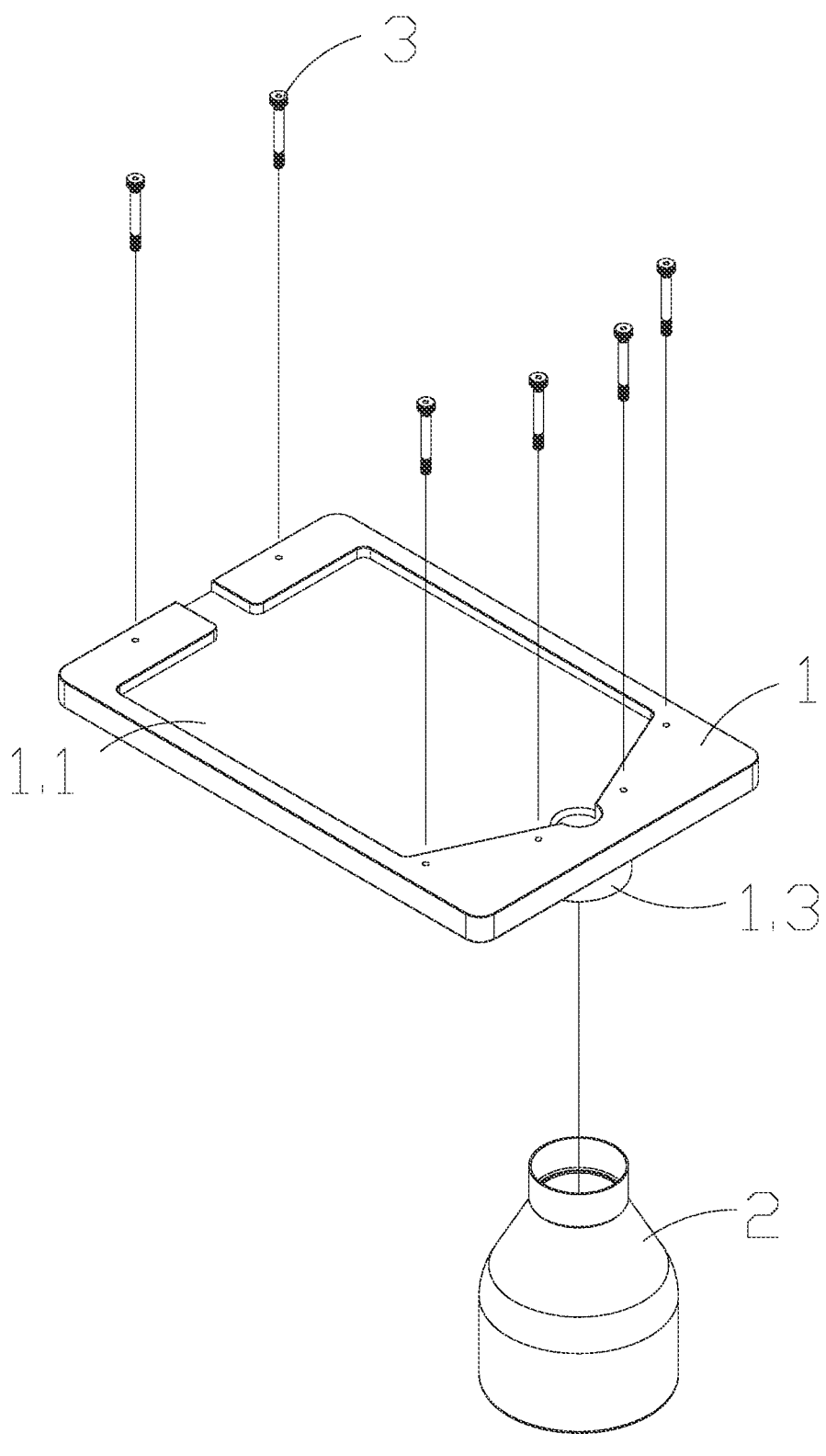
FIG. 1 is a schematic exploded view of the structure of the fast-connected laboratory animal test bench provided by the embodiment of the present application.
Figure 2:
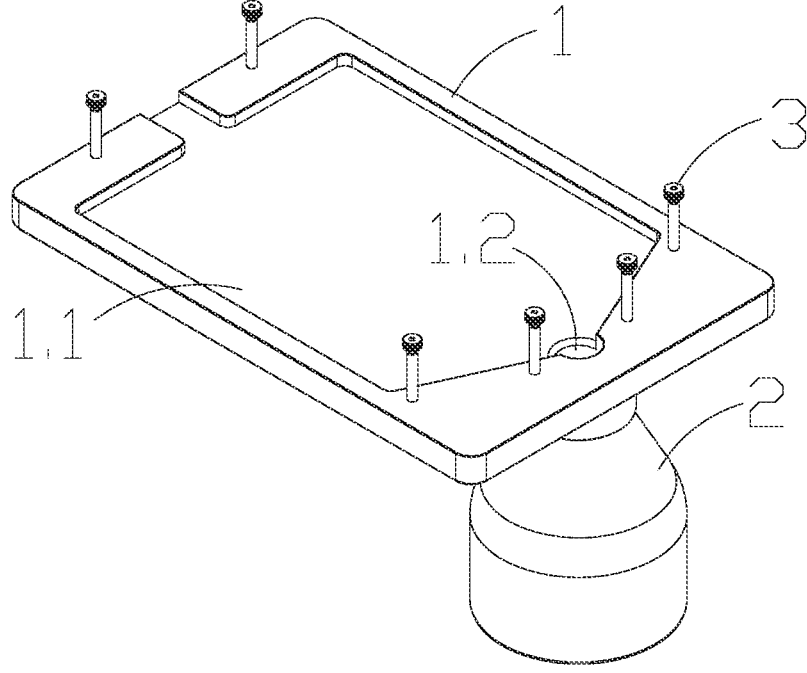
FIG. 2 is the axonometric view of the fast-connected laboratory animal test bench structure provided by the embodiment of the present application.

1 Test bench; 1.1 Liquid discharge groove; 1.2 Liquid discharge port; 1.3 Connecting piece; 1.3.1 Annular ring; 1.3.2 Lug; 1.3.3 Internally threaded sleeve; 1.4 Bolt fixing hole; 2 Liquid storage tank; 3 Fixing bolt.

DETAILED DESCRIPTION

The technical solution in the embodiment of the present application will be clearly and completely described below in conjunction with the drawings in the embodiment of the application. Apparently, the described embodiments are only some of the embodiments of the present application, not all of them.

Please refer to FIG. 1-FIG. 8, the present application provides a fast-connected laboratory animal test bench, comprising a test bench 1 and a liquid storage tank 2 and a plurality of fixing bolts 3, and the fixing bolts 3 are all arranged on the test bench 1, and is able to bind ropes to fix animals, that is, after the animal is bound and fixed by the rope, the outer end of the rope is fixed on the corresponding fixing bolt 3, thereby realizing the fixation of the animal. The test bench 1 is provided with a discharge groove 1.1 located inside a range surrounded by all the fixing bolts 3, the liquid storage tank 2 is arranged at bottom of the test bench 1 and is configured to accommodate waste liquid discharged from the liquid discharge groove 1.1. During the test, the remaining waste liquid waste will be discharged into the liquid storage tank 2 through the discharge groove 1.1, thereby ensuring the cleanliness of the test bench 1 and facilitating the rapid recovery of the test environment.

As shown in FIG. 1, the fixing bolt 3 is divided into an upper and a lower section, an outer wall of the lower section is provided with external threads, and an outer wall of the upper section is configured to be smooth, and a plurality of bolt fixing holes 1.4 are correspondingly formed on the test bench 1, the lower section of the fixing bolt 3 is screwed into the corresponding bolt fixing hole 1.4. After the fixing bolt 3 is fixed to the test bench 1 through the bolt fixing hole 1.4, it can be equivalent to the effect of the fixing pile, which facilitates the binding of the rope.

A liquid discharge port 1.2 communicating with the liquid discharge groove 1.1 is formed in the test bench 1, and the waste liquid in the liquid discharge groove 1.1 is led to the inside of the liquid storage tank 2 through the liquid discharge port 1.2. Specifically, the liquid discharge port 1.2 is used as an intermediate connection hole, which is beneficial to quickly lead the waste liquid accumulated in the liquid discharge groove 1.1 to the liquid storage tank 2 through the liquid discharge port 1.2, so as to realize the collection and cleaning of the waste liquid.

An annular protrusion is provided at an outer edge of a bottom end surface of the test bench 1 around the liquid discharge port 1.2, and a connecting piece 1.3 located on an outer periphery of the annular protrusion is arranged on the bottom end surface of the test bench 1, an outer wall of a bottle mouth of the liquid storage tank 2 is provided with external threads, and is screwed with the connecting piece 1.3 through the external threads. The connecting piece 1.3 is convenient for fixing the liquid storage tank 2 on the test bench 1, so that the liquid waste on the test bench 1 is quickly discharged into the liquid storage tank 2.

Figure 3:
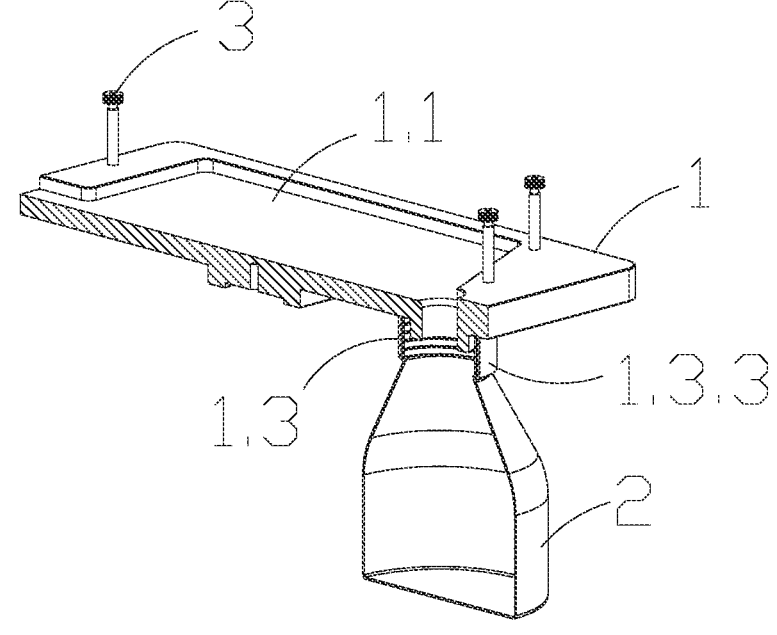
FIG. 3 is a half-sectional view of the structure of FIG. 2 provided in the embodiment of the present application.
Figure 4:
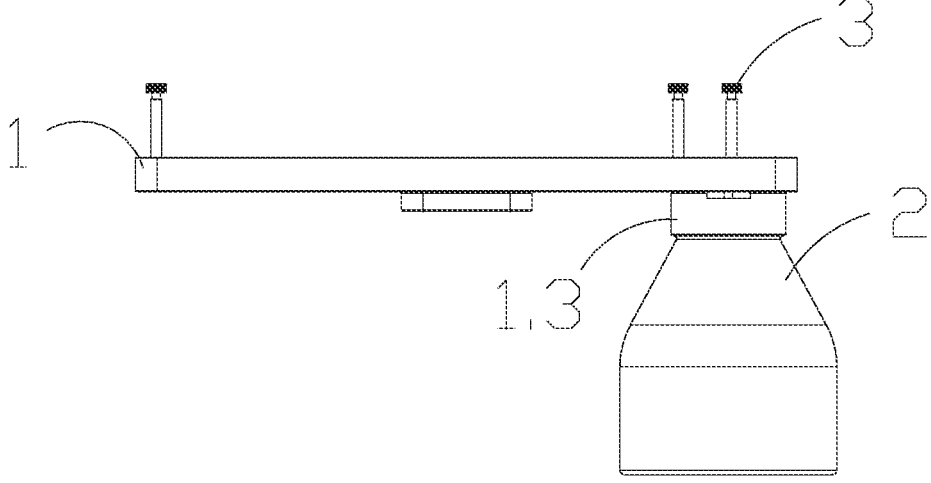
FIG. 4 is one of the schematic diagrams of the planar structure of the fast-connected laboratory animal test bench provided by the embodiment of the present application.
Figure 5:
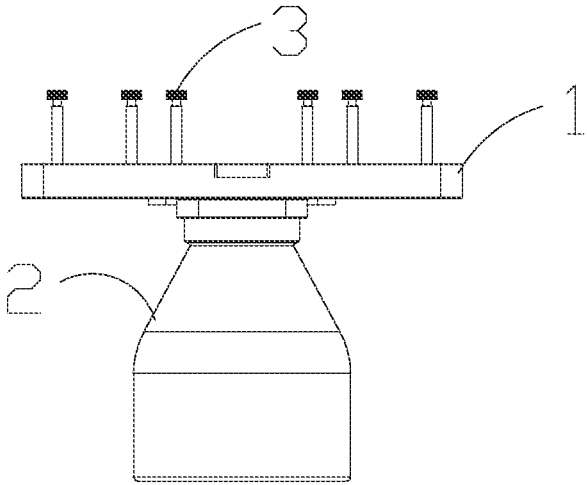
FIG. 5 is the second schematic diagram of the planar structure of the fast-connected laboratory animal test bench provided by the embodiment of the present application.
Figure 6:
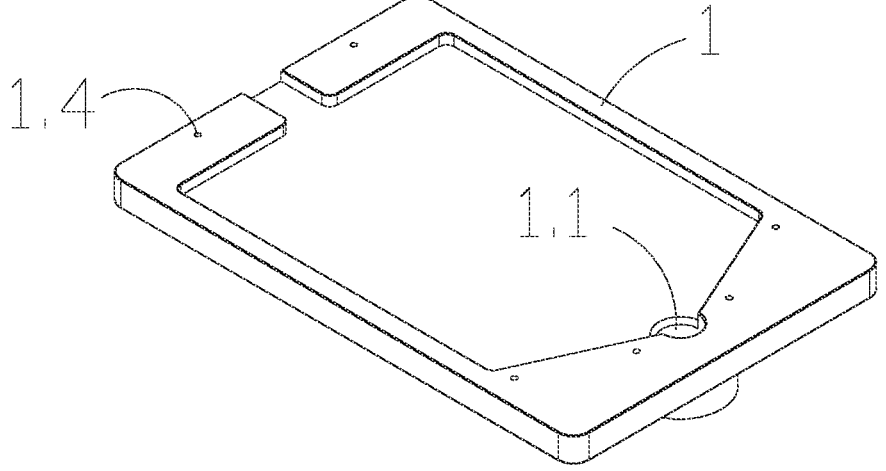
FIG. 6 is an axonometric view of the test bench structure provided by the embodiment of the present application.
Figure 8:
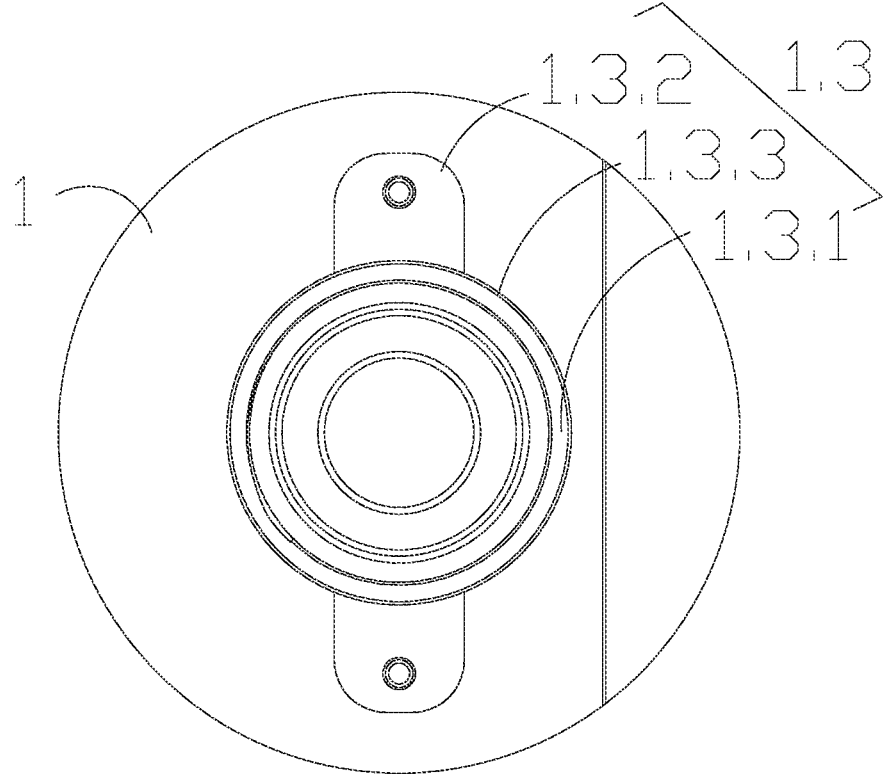
FIG. 8 is a partial enlarged view of A in FIG. 7 provided by the embodiment of the present application.

As shown in FIG. 3 and FIG. 8, specifically, the connecting piece 1.3 comprises:

an annular ring 1.3.1, located on the outer periphery of the annular protrusion;

two lugs 1.3.2, connected to both symmetrical sides of the annular ring 1.3.1, and fixed to the bottom end surface of the test bench 1;

two internally threaded sleeves 1.3.3, respectively connected to an inner and outer sides of an outer surface of the annular ring 1.3.1, there is a distance between the internally threaded sleeves, and there is also a distance between the internally threaded sleeve 1.3.3 located on the inner side and an outer ring of the annular protrusion, the bottle mouth of the liquid storage tank 2 is connected with one of the internally threaded sleeves 1.3.3.

When the connecting piece 1.3 is operated, the lugs 1.3.2 are fixed to the bottom end surface of the test bench 1 by screws, and the two internally threaded sleeves 1.3.3 after fixing are located on the outer ring of the annular protrusion and do not contact it. The bottle mouth of the liquid storage tank 2 can be screwed with the inner ring of the matching internally threaded sleeve 1.3.3. On the contrary, it is to use the design of two internally threaded sleeves 1.3.3 to facilitate the installation of different liquid storage tanks 2, and the installation applicability is higher.

The test bench 1 is formed in the shape of a rectangular plate, and the four corners are rounded and chamfered. The discomfort caused by the user accidentally bumping into the corner of the test bench is reduced.

Figure 7:
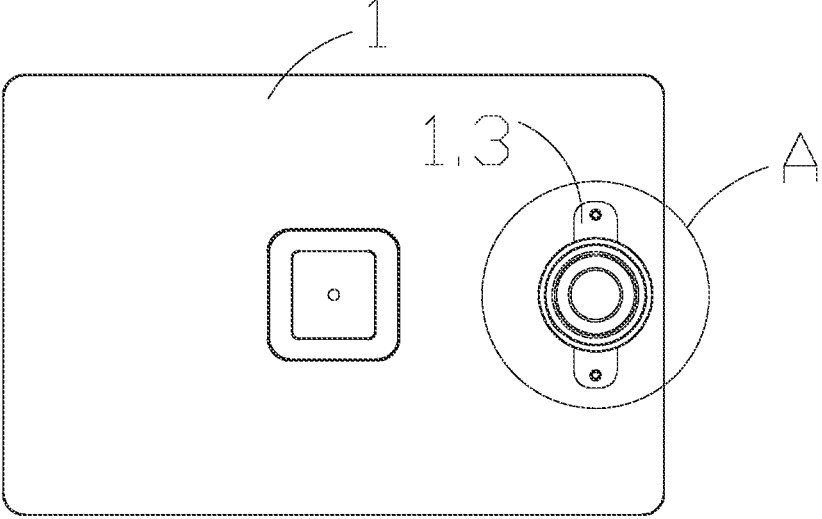
FIG. 7 is a bottom view of the test bench structure provided by the embodiment of the present application.

As shown in FIG. 3 and FIG. 7, at a middle position of the bottom of the test bench 1 is provided with rectangular bumps integrally formed with it, and a mounting groove is arranged inside the rectangular bump, and a vertical cross-sectional shape of the mounting groove is an inverted T-shape. The external legs can be inserted into the mounting grooves of the rectangular bumps to facilitate the fixing of the test bench 1. The shape of the specific external leg design may include the shape of the base and the middle column. The middle column is fixed in the middle of the upper end of the base, and the shape of the top of the middle column is adapted to the mounting groove. Other suitable shapes can also be selected for the external legs, which are not limited here.

When using the present application:

The animals to be tested are tied up with ropes, and the ropes are bound to the fixing bolts 3. The bound animals are located above the liquid discharge groove 1.1 on the upper part of the test bench 1. During the animal experiment, the residual liquid waste will fall directly into the discharge groove 1.1 and collect into the liquid storage tank 2 through the liquid discharge port 1.2. The overall structure is relatively simple, and the cleaning of waste liquid and waste on the test bench 1 is realized.

It will be obvious to a person skilled in the art that the application is not limited to the details of the exemplary embodiments described above. The present application can be implemented in other specific forms without departing from the spirit or essential characteristics of the present application. Therefore, the embodiments should be regarded as exemplary rather than restrictive in every respect. The scope of the present application is defined by the appended claims rather than the above description, and all changes that come within the meaning and range of equivalency of the claims are intended to be embraced therein. Any reference sign in a claim should not be construed as limiting the claim concerned.

What is claimed is:

1. A quick-connected laboratory animal test bench, comprising a test bench (1) and a liquid storage tank (2) and a plurality of fixing bolts (3), and the fixing bolts (3) are all arranged on the test bench (1), and is able to bind ropes to fix animals, the test bench (1) is provided with a discharge groove (1.1) located inside a range surrounded by all the fixing bolts (3), the liquid storage tank (2) is arranged at a bottom of the test bench (1) and is configured to accommodate waste liquid discharged from the liquid discharge groove (1.1), a liquid discharge port (1.2) communicating with the liquid discharge groove (1.1) is formed in the test bench (1), and the waste liquid in the liquid discharge groove (1.1) is led to the inside of the liquid storage tank (2) through the liquid discharge port (1.2), an annular protrusion is provided at an outer edge of a bottom end surface of the test bench (1) around the liquid discharge port (1.2), and a connecting piece (1.3) located on an outer periphery of the annular protrusion is arranged on the bottom end surface of the test bench (1), an outer wall of a bottle mouth of the liquid storage tank (2) is provided with external threads, and is screwed with the connecting piece (1.3) through the external threads, the connecting piece (1.3) comprises:

an annular ring (1.3.1), located on the outer periphery of the annular protrusion;

two lugs (1.3.2), connected to both symmetrical sides of the annular ring (1.3.1), and fixed to the bottom end surface of the test bench (1);

two internally threaded sleeves (1.3.3), respectively connected to an inner and outer sides of an outer surface of the annular ring (1.3.1), there is a distance between the internally threaded sleeves, and there is also a distance between the internally threaded sleeve (1.3.3) located on the inner side and an outer ring of the annular protrusion, the bottle mouth of the liquid storage tank (2) is connected with one of the internally threaded sleeves (1.3.3).

2. The quick-connected laboratory animal test bench according to claim 1, wherein the fixing bolt (3) is divided into an upper and a lower section, an outer wall of the lower section is provided with external threads, and an outer wall of the upper section is configured to be smooth, and a plurality of bolt fixing holes (1.4) are correspondingly formed on the test bench (1), the lower section of the fixing bolt (3) is screwed into the corresponding bolt fixing hole (1.4).

3. The quick-connected laboratory animal test bench according to claim 1, wherein the test bench (1) is formed in the shape of a rectangular plate, and the four corners are rounded and chamfered.

4. The quick-connected laboratory animal test bench according to claim 1, wherein at a middle position of the bottom of the test bench (1) is provided with rectangular bumps integrally formed with it, and a mounting groove is arranged inside the rectangular bump, and a vertical cross-sectional shape of the mounting groove is an inverted T-shape.

* * * * *